United States Patent
Strueber et al.

(10) Patent No.: US 9,492,600 B2
(45) Date of Patent: Nov. 15, 2016

(54) INTRAVASCULAR BLOOD PUMP AND METHOD OF IMPLANTATION

(75) Inventors: Martin Strueber, Hannover (DE); Lisa Ensz, Boston, MA (US)

(73) Assignee: HeartWare, Inc., Miami Lakes, FL (US)

(*) Notice: Subject to any disclaimer, the term of this patent is extended or adjusted under 35 U.S.C. 154(b) by 0 days.

(21) Appl. No.: 13/469,925

(22) Filed: May 11, 2012

(65) Prior Publication Data

US 2013/0066421 A1    Mar. 14, 2013

Related U.S. Application Data (60) Provisional application No. 61/485,856, filed on May 13, 2011.

(51) Int. Cl.
  *A61M 1/12*   (2006.01)
  *A61F 2/24*   (2006.01)
  *A61M 1/10*   (2006.01)

(52) U.S. Cl.
  CPC ............... *A61M 1/125* (2014.02); *A61F 2/24* (2013.01); *A61M 1/101* (2013.01); *A61M 1/1031* (2014.02); *A61F 2/2481* (2013.01); *A61M 1/1037* (2013.01); *A61M 1/12* (2013.01); *A61M 1/122* (2014.02)

(58) Field of Classification Search
  CPC .................... A61M 1/101; A61M 1/12; A61M 1/1037; A61M 1/1081; A61M 1/122; A61M 1/125; A61M 1/127; A61F 2/2481
  USPC ............ 623/3.1, 3.13, 3.15, 3.24, 3.25, 3.27
  See application file for complete search history.

(56) References Cited

U.S. PATENT DOCUMENTS

| | | | |
|---|---|---|---|
| 4,753,221 A | 6/1988 | Kensey et al. | |
| 4,906,229 A | 3/1990 | Wampler | |
| 5,112,349 A | 5/1992 | Summers et al. | |
| 5,147,388 A * | 9/1992 | Yamazaki | A61M 1/101 600/16 |
| 5,290,227 A | 3/1994 | Pasque | |
| 5,911,685 A * | 6/1999 | Siess | A61M 1/101 415/900 |

(Continued)

FOREIGN PATENT DOCUMENTS

| | | |
|---|---|---|
| CN | 101282748 A | 10/2008 |
| WO | 2007040663 A1 | 4/2007 |

OTHER PUBLICATIONS

International Search Report issued by the International Searching Authority (ISA/US) on Aug. 24, 2012 in connection with International Application No. PCT/US2012/037596.

(Continued)

*Primary Examiner* — Christian Sevilla
*Assistant Examiner* — Seema Mathew
(74) *Attorney, Agent, or Firm* — Lerner, David, Littenberg, Krumholz & Mentlik, LLP (57) ABSTRACT

A blood pump is implantable within the vasculature, such as within the pulmonary artery. The pump may project through a native valve such as the pulmonary valve. In use, the pump opposes retrograde flow and thus acts as a replacement for the native valve. The pump may be an axial flow pump having a generally tubular housing adapted to fit within the space proximal to the bifurcation of the pulmonary artery while projecting only slightly proximally of the annulus of the native pulmonary valve.

16 Claims, 5 Drawing Sheets

(56) References Cited

U.S. PATENT DOCUMENTS

| | | | |
|---|---|---|---|
| 6,093,001 | A | 7/2000 | Burgreen |
| 6,190,319 | B1 * | 2/2001 | Goldowsky ......... A61M 1/1081 |
| | | | 600/16 |
| 6,248,091 | B1 * | 6/2001 | Voelker ................ A61M 1/101 |
| | | | 604/151 |
| 6,290,639 | B1 * | 9/2001 | Mussivand ......... A61M 1/1037 |
| | | | 600/16 |
| 6,443,884 | B1 * | 9/2002 | Miyawaki ........... A61M 1/1086 |
| | | | 600/17 |
| 7,942,805 | B2 | 5/2011 | Shambaugh, Jr. |
| 8,007,254 | B2 | 8/2011 | LaRose et al. |
| 9,265,870 | B2 * | 2/2016 | Reichenbach ........ A61M 1/101 |
| 9,345,824 | B2 * | 5/2016 | Mohl .................. A61M 1/1086 |
| 2004/0171905 | A1 | 9/2004 | Yu et al. |
| 2005/0049696 | A1 | 3/2005 | Siess et al. |
| 2005/0107657 | A1 * | 5/2005 | Carrier ................ A61M 1/101 |
| | | | 600/16 |
| 2007/0100196 | A1 | 5/2007 | LaRose et al. |
| 2007/0134993 | A1 | 6/2007 | Tamez et al. |
| 2007/0156006 | A1 * | 7/2007 | Smith ................... A61M 1/101 |
| | | | 600/16 |
| 2009/0203957 | A1 | 8/2009 | LaRose et al. |
| 2010/0249489 | A1 * | 9/2010 | Jarvik ................. A61F 2/2412 |
| | | | 600/16 |
| 2011/0311383 | A1 | 12/2011 | White |
| 2014/0100413 | A1 * | 4/2014 | Casas ................... A61M 1/101 |
| | | | 600/16 |
| 2014/0128967 | A1 * | 5/2014 | Jarvik ................. A61F 2/2418 |
| | | | 623/2.17 |
| 2014/0357937 | A1 * | 12/2014 | Reyes .................. A61M 1/101 |
| | | | 600/17 |
| 2015/0141739 | A1 * | 5/2015 | Hsu ..................... A61M 1/1024 |
| | | | 600/16 |

OTHER PUBLICATIONS

Written Opinion of the International Searching Authority issued by the International Searching Authority (ISA/US) on Aug. 24, 2012 in connection with International Application No. PCT/US2012/037596.

International Preliminary Report on Patentability issued by the International Bureau of WIPO on Nov. 19, 2013 in connection with International Application No. PCT/US2012/037596.

Extended European Search Report for Application No. 12786270.4 dated Sep. 15, 2014.

European Office Action for Application No. 12786270.4 dated Jul. 10, 2015.

Westaby S et al: "Adult human valve dimensions and their surgical significance", American Journal of Cardiology, vol. 53, No. 4, Feb. 1, 1984, pp. 552-556.

Chinese Office Action for Application No. 201280023831.X dated Feb. 25, 2015.

* cited by examiner

FIG. 5B

INTRAVASCULAR BLOOD PUMP AND METHOD OF IMPLANTATION

CROSS-REFERENCE TO RELATED APPLICATIONS

The present application claims the benefit of the filing date of U.S. Provisional Patent Application No. 61/485,856 filed May 13, 2011, the disclosure of which is incorporated herein by reference.

BACKGROUND OF THE INVENTION

Implantable intravascular blood pumps are typically used in the later stages of heart disease or after trauma to the heart, when the heart itself is too weak or otherwise incapable of creating sufficient blood pressure and blood circulation to satisfy body function.

Various blood pumps are already in use for the purpose of augmenting or replacing the blood pumping action of damaged or diseased hearts. Blood pumps are commonly used in three situations: (1) for acute support during cardio-pulmonary operations; (2) for short-term support while awaiting recovery of the heart from surgery; or (3) as a bridge to keep a patient alive while awaiting heart transplantation. The pumps may be designed to provide at least one of right or left ventricular assist.

Implantable blood pumps comprise miniaturized pumps capable of being percutaneously or surgically introduced into or adjacent to the vascular system of a patient, typically to provide left or right heart support, or even total heart support. Various types of blood pumps include radial flow centrifugal pumps and axial flow pumps. Examples of axial flow heart pumps are disclosed in co-pending, commonly assigned, U.S. Published Application Nos. 20090203957 (the 957 Publication) and 20110311383 (the '383 Publication) and U.S. Pat. No. 8,007,254 (the '254 patent), the entireties of which are hereby incorporated by reference herein as if fully set forth herein.

Axial flow pumps are commonly implanted within a chamber of the heart, such as is disclosed in the '746 Application. This placement of the pump in the particular chamber effectively immerses the pump within the blood to provide direct pumping support to the particular chamber. However, such placement also decreases the volume of the particular chamber which is available for blood capacity.

In an attempt to remedy this issue, there have been attempts to position a portion of a blood pump through a heart valve or vessel connected to one of the chambers of the heart, while maintaining valve structure and/or function, as is illustrated in U.S. Pat. Nos. 4,753,221 and 5,112,349. However, such positioning may result in insufficient pumping and potential leakage around the pump, may cause unintended damage to the heart valve, and may further present difficulties in stabilizing the pump within the anatomy.

While current implantable blood pump placement, within a chamber of the heart, provides numerous benefits to patients in need thereof, alternative placements may provide additional benefits to patients, in addition to potentially making such devices available to an even wider range of patients in need thereof. Additionally, improved methods and devices for placement of a blood pump outside of a chamber of the heart, such as through a valve, are needed to provide a plausible alternative pump placement.

BRIEF SUMMARY OF THE INVENTION

One aspect of the present invention provides an implantable blood pump apparatus including a blood pump. The blood pump desirably has a substantially tubular casing having proximal and distal ends and a length therebetween. The tubular casing preferably has a first outer diameter along at least a portion of the length between the first and second ends. The pump also desirably has a flow path extending through the tubular casing and along the length of the casing, a rotor within the flow path, and a stator for driving the rotor. Preferably, an electrical connection adapted to connect to a power source is provided. The electrical connection desirably extends from the tubular casing in a direction transverse to the flow path. The electrical connection desirably extends from the casing remote from the proximal and distal ends thereof. The apparatus may also include a pump attachment device. Where the pump attachment device includes two sewing rings, the electrical connection may extend from the tubular casing at a position between the two sewing rings when the pump is implanted. Additionally, as the apparatus is adapted to be positioned within a vasculature, the electrical connection may extend transverse from the tubular casing to a position outside of the vasculature when the pump is implanted.

A further aspect of the invention provides a method of implanting a blood pump. A method according to this aspect of the invention desirably includes securing a blood pump within a native heart valve space of a patient such that a portion of the blood pump is positioned within a native heart valve annulus and wherein the portion of the pump forces native valve leaflets to a substantially open position such that the native valve leaflets abut surrounding tissues and are substantially retained against opening and closing motion. Further, there may be a seal around the blood pump substantially blocking flow around the pump. In one example, the native heart valve space includes a portion of a pulmonary artery having a pulmonary valve and extending between a bifurcation of the pulmonary artery in a distal direction and a right ventricle of a heart in a proximal direction. Prior to the securing step, the method may further includes accessing the native heart valve space by forming a cut in a sidewall of the portion of the pulmonary artery and approaching the pulmonary valve from the distal direction. The portion of the blood pump positioned through the annulus may force native valve leaflets to an open position in a retrograde direction. The blood pump may be secured within the native heart valve space by utilizing a pump attachment device, wherein the pump attachment device is one of an at least one sewing ring, a felt ring or a felt strip. In one example, the at least one sewing ring may be two sewing rings. The step of forming the cut in the sidewall may include severing the portion of the pulmonary artery to form two cut ends of the pulmonary artery. One of the sewing rings may then be implanted onto or adjacent to each cut end. Sutures may be used to implant the sewing rings. Further, the blood pump may be secured to both sewing rings. Alternatively, if a felt strip is used, the felt strip may be secured to the blood pump prior to the step of securing the blood pump in the native heart valve space, such that the step of securing the blood pump in the native heart valve space further comprises suturing the felt strip to at least one of the pulmonary valve and the portion of the pulmonary artery.

In yet a further embodiment, the present invention may include a method for implanting a blood pump into a portion of a pulmonary artery including a pulmonary valve and extending between a bifurcation of the pulmonary artery in a distal direction and a right ventricle of a heart in a proximal direction, the method comprising securing the blood pump so that the blood pump is positioned proximal to the bifurcation and extends through the pulmonary valve, wherein, once secured, the blood pump extends proximally into the conus arteriosus of the right ventricle but not beyond the conus arteriosus. The blood pump may be secured within the portion of the pulmonary artery by utilizing a pump attachment device, wherein the pump attachment device is one of an at least one sewing ring, a felt ring or a felt strip. Prior to the step of securing the blood pump and pump attachment device, the method may further include positioning the blood pump and pump attachment device into the pulmonary artery and the blood pump through the pulmonary valve, wherein upon positioning the blood pump through the pulmonary valve, the blood pump forces native valve leaflets of the pulmonary valve to a substantially open position such that the native valve leaflets abut surrounding tissues and are substantially retained against opening and closing motion. Further, the portion of the blood pump positioned through the pulmonary valve may force native valve leaflets to an open position in a retrograde direction. The at least one sewing ring may include two sewing rings. Additionally, prior to the securing step, the method may further include accessing the portion of the pulmonary artery by forming a cut in a sidewall of the portion of the pulmonary artery distal to the pulmonary valve, wherein forming the cut includes severing the portion of the pulmonary artery to form two cut ends of the portion of the pulmonary artery. One sewing ring may be implanted onto or adjacent to each cut end. The blood pump may then be secured to both sewing rings.

DETAILED DESCRIPTION

The term "implantable blood pump" or "blood pump" as used herein, refers to a blood pump which is capable of being implanted and used within the vasculature, such as within the heart, the aorta, the various arteries or veins, or the like. One such example of an implantable blood pump for use in the present invention may be an axial flow ventricular assist device (VAD), or other pump which is implantable into a patient in need thereof.

As used herein, the term "native heart valve space" is intended to refer to the location and anatomy of a native heart valve in a vasculature of a patient. A native heart valve space includes, for example, a native valve annulus, at least two native valve leaflets, associated tissue such as the surrounding and adjacent tissues including a sidewall of the vasculature, and the like. A native heart valve space of an aortic or pulmonary extends up to, but does not include, a chamber of the heart. For example, a pulmonary heart valve space includes a portion of a pulmonary artery including a pulmonary valve and extending between a bifurcation of the pulmonary artery in a distal direction and the right ventricle of the heart in a proximal direction. Thus, the pulmonary heart valve space does not include, for example, the conus arteriosus of the right ventricle.

Figure 1:
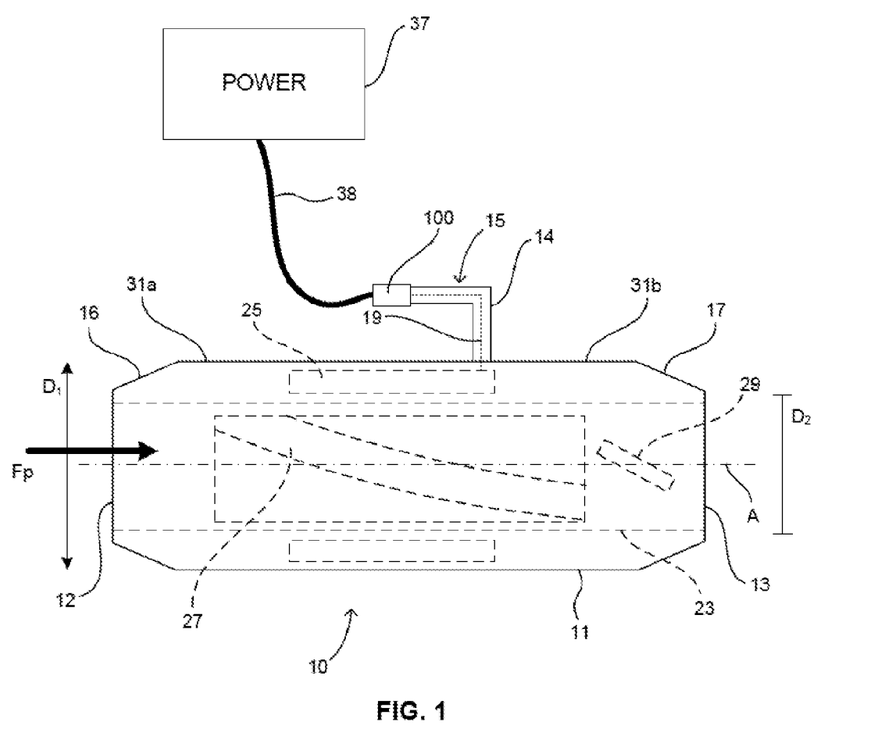
FIG. 1 is a diagrammatic elevational view depicting an axial-flow blood pump according to one embodiment of the present invention.

A blood pump 10 according to one embodiment of the invention is illustrated in FIG. 1. Blood pump 10 has an outer, generally cylindrical tubular casing 11 with a proximal end 12, a distal end 13. The pump also has a flow path Fp defined by an internal casing 23 extending between these ends. The blood pump is electrically powered and uses magnetic or electromagnetic forces, for example, to power a magnetic rotor placed within or adjacent to the flow path of blood moving into or out of the heart. An at least one electromagnet, or stator 25 schematically depicted in broken lines, is positioned outside of flow path Fp, whereas the rotor 27 is disposed within the flow path Fp. In this illustrated embodiment, the stator is isolated from the flow path Fp by internal casing 23, such that the stator is positioned between outer casing 11 and internal casing 23.

Rotor 27 is magnetic. The stator typically is a set of electrically conductive wire coils. The stator is energized by a power source with alternating currents through the coils to create a rotating magnetic field. That is, the field is directed transverse to the axis A of the tubular casing and flow path, and the direction of the field rotates about this axis. As the field rotates, the rotor spins about its central axis (substantially coincident with the central axis of the tubular casing) thus advancing the blood within the flow path. During operation, the rotor desirably is suspended within internal casing 23 by magnetic and hydrodynamic forces. A flow smoothing structure 29 may be provided between rotor 27 and the distal end of the flow path to convert rotational momentum of the blood into useful pumping work and thereby increase the efficiency of the pump. The internal components of the blood pump 10, such as the internal casing 23, rotor 27, stator 25 and flow smoothing structure 29, are in many respects similar to those found in the '957 Publication, as well as in the MVAD™ blood pump (HeartWare International, Inc., Miami Lakes, Fla.). The blood pump 10 is intended to support the full cardiac output of the heart, which is generally, for example, about 7 liters/minute to about 8 liters/minute, though this range may potentially be higher (up to, for example, 10 liters/minute) for larger patients with higher blood flows. The pump desirably has the capacity to provide these flow rates against a pressure differential opposing flow up to the normal systolic pressure in the pulmonary circulation, but desirably is controllable to deliver a lower flow, lower pressure or both.

The exterior surface of outer casing 11 includes a central section 31 which is of uniform diameter D1 and tapered, conical end portions 16 and 17 at the proximal end 12 and distal end 13 respectively. Thus, the exterior surface tapers inwardly from diameter D1, also referred to as the major diameter of the housing, to a minor diameter D2, just slightly larger than the diameter of the flow path, at each end. A hollow cable housing 15 includes a leg 14 projecting outwardly from the central section 31 of the housing in a direction transverse to the axis A of the housing and desirably perpendicular to the axis A. Leg 14 is disposed remote from the ends of the housing and remote from conical sections 16 and 17. Thus, there is a proximal portion 31a of central section between leg 14 and conical section 16 and a distal portion of the central section between leg 14 and a distal portion 31*b* between leg 14 and conical section 17. In this embodiment, the cable housing also includes a leg projecting transverse to leg 14 and parallel to axis A, in the direction toward the proximal end 12 of the housing. Although the legs are depicted in FIG. 1 as joining one another at a sharp corner, they desirably join one another at a gradually radiused bend in practice. The cable housing contains electrical wiring 19 which is directly or indirectly connected to the stator 25. The end of cable housing 15 holds a connector 100 electrically connected to the wiring 19. The cable housing and wiring thus provide an electrical connection extending from the outer casing of the pump transverse to the axis A and transverse to the flow path.

Pump 10 may have dimensions suitable for implantation into a particular native heart valve space. For example, pump 10 may have a length substantially the same as or smaller than that of the pulmonary heart valve space (i.e., the length of the pulmonary artery 160 depicted in FIG. 3B). The pump 10, suitable for use in the pulmonary artery and valve, may have a major diameter $D_1$ of the tubular casing, of about 2 cm to about 3 cm. The tubular casing, and hence the pump 10 as a whole, desirably has a length in the axial direction of about 5 cm or less, preferably 4 cm to about 5 cm, such as about 4.5 cm. Major diameter $D1$ is the largest dimension of the pump excluding the cable housing. Of course, these dimensions are only exemplary and other dimensions suitable for implantation into vasculature of a patient are also envisioned.

The blood pump is used in cooperation with an electrical power source 37 which may be implanted somewhere within the body of the patient or may be external to the patient, as is known in the art. In use, a cable 38 having a connector 100 adapted to engage the connector in cable housing 15 electrically connects the power source to the pump.

Figure 2B:
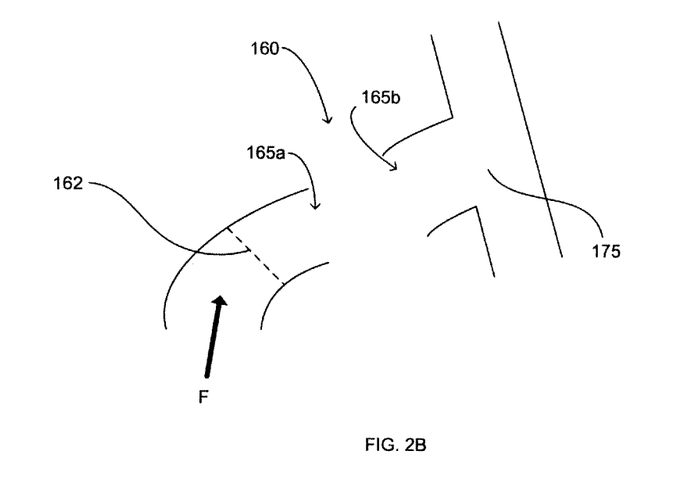
FIG. 2B is a view similar to FIG. 2A but depicting the pulmonary valve space during one step of a pump positioning method according to one embodiment of the invention.
Figure 3A:
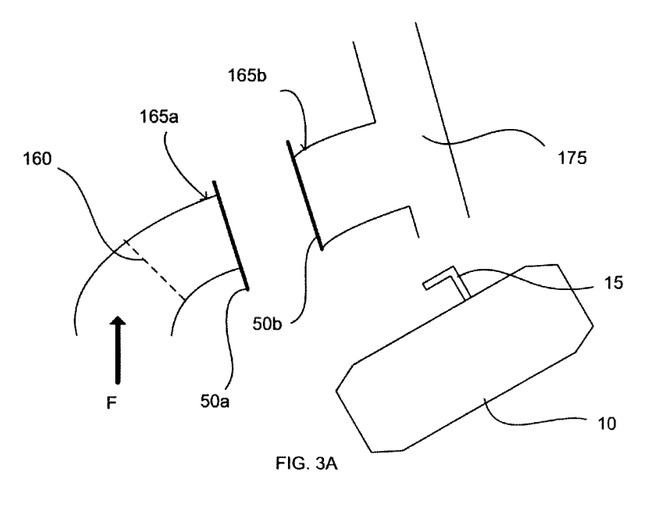
FIGS. 3A and 3B are views similar to FIGS. 2A and 2B but depicting later steps of the pump positioning method of FIG. 2B.
Figure 3B:
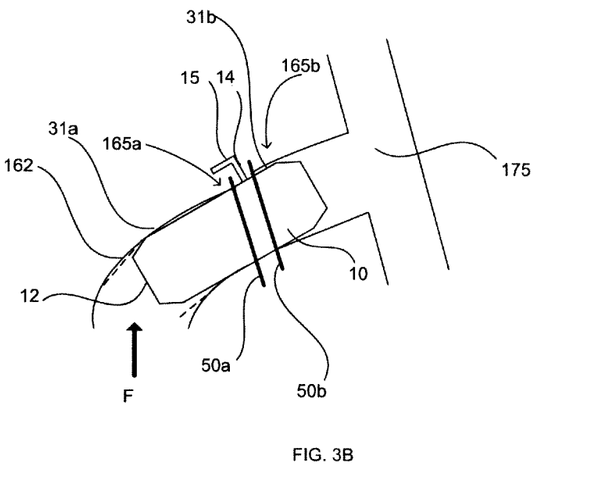

As further discussed below, when the pump is implanted, the cable housing 15 directs the wiring out of the vasculature, such as pulmonary artery 160 (see FIG. 3B) for connection with power source 37 (FIG. 1). The cable housing 15 may extend through a sidewall of the vasculature or through a formed cut (as in FIG. 2B, 3B, 5B, discussed below) within the vasculature in order to extend outside of the vasculature. The apparatus also includes a pump attachment device to secure the blood pump to the surrounding tissue, such as in a native heart valve space. The pump attachment device, as illustrated in FIGS. 3A-3B, may include at least one sewing ring 50*a*. Preferably, the pump attachment device 50 may include two sewing rings 50*a*, 50*b*. Examples of such sewing rings are disclosed in U.S. Publication No. 2004/0171905 (the '905 Publication) and U.S. Pat. No. 7,942,805 (The '805 patent), the entireties of which are incorporated by reference herein as if fully set forth herein. As disclosed in the '905 Publication, the sewing ring includes an annular fabric having a hollow center. As described in the '805 patent, a sewing ring may further include a clamping device in the form of central cylindrical ring portion secured to the annular fabric and coaxial therewith. The ring portion includes a fixed wall portion and a movable wall portion. The sewing ring may further include a clamping device such as a screw clamp for urging the movable wall portion toward the fixed wall portion. The sewing ring is adapted to be secured to the tissue, such as the sidewall of the vasculature, for example by suturing the annular fabric to the wall of an artery around the periphery of the artery. Once a pump is placed within the sewing ring structure, the movable wall can be tightened, using a screw connection or the like, to clamp the central cylindrical ring portion around the pump to secure the pump to the sewing ring.

In a method according to one embodiment of the present invention, pump 10 is implanted in a native heart valve space incorporating a portion of a pulmonary artery 160 including a pulmonary valve 162 and extending between a bifurcation 175 of the pulmonary artery in a distal direction and a right ventricle 170 (schematically shown in FIG. 2 and better depicted in FIG. 4) of a heart in a proximal direction. The right ventricle includes a generally conical portion 163 known as the conus arteriosus just proximal to the annulus of pulmonary valve 162. The natural flow of blood in the distal direction is indicated by arrow F. As discussed below, the method includes securing the blood pump 10 so that the blood pump is positioned proximal to the bifurcation and extends through the pulmonary valve. The blood pump desirably extends only minimally, if at all, proximally to the annulus of the pulmonary valve. For example, the proximal end of the blood pump desirably extends about 2 cm or less, and desirably about 1 cm or less, proximally to the annulus of the pulmonary valve. For example, the blood pump may extend into the conus arteriosus of the right ventricle, but desirably does not extend beyond the conus arteriosus. The blood pump 10 is secured within the portion of the pulmonary artery 160 using a pump attachment device, such as at least one sewing ring 50*a*, and preferably two sewing rings 50*a*, 50*b*.

Figure 2A:
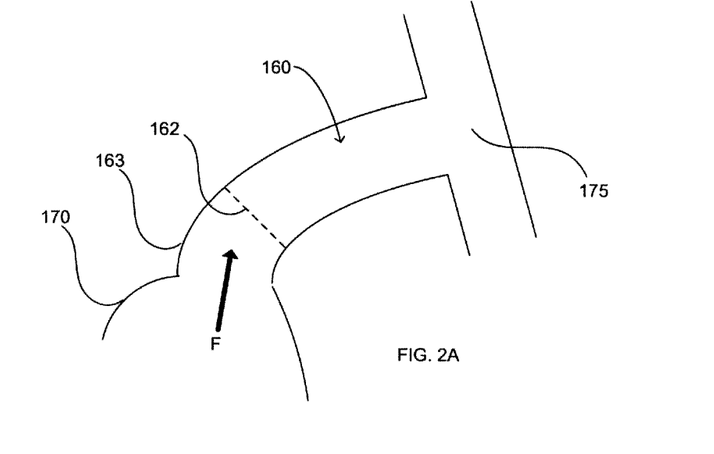
FIG. 2A is a simplified schematic view of a native pulmonary valve space.

In the procedure, the pulmonary artery 160 is accessed via an open-chest procedure and the patient is placed on heart and lung bypass, as is known in the art. As illustrated in FIGS. 2A-B, prior to the step of securing the blood pump within the portion of the pulmonary artery, a cut is formed in the portion of the pulmonary artery 160. The cut may be formed through at least a portion of the sidewall of the portion of the pulmonary artery 160. In this example, the cut may be made about 2.5 cm distal to the pulmonary valve, though this measurement may differ depending on particular anatomy. As illustrated in FIG. 2B, the cut may completely or partially sever the portion of the pulmonary artery to form two cut ends 165*a*, 165*b*. Continuing with the method as illustrated in FIG. 3A, the two sewing rings 50*a*, 50*b* may be implanted onto or adjacent to the cut ends 165*a*, 165*b*. The sewing rings may be implanted onto the tissue of the pulmonary artery in any manner desired, though the use of sutures is preferred. The blood pump 10 may then be directed into the surgical site.

FIG. 3B illustrates the step of implanting the blood pump 10 into the portion of the pulmonary artery 160. The pump is positioned proximally through the sewing ring 50*a* and through the pulmonary valve 162. As the proximal end 12 of the blood pump is positioned into and through the valve 162, the blood pump may force native valve leaflets of the pulmonary valve in the proximal or retrograde direction, opposite to flow direction F. The valve leaflets are thus brought to a substantially open position such that the native valve leaflets abut surrounding tissues of the portion of the pulmonary artery 160 and are substantially retained against opening and closing motion. Although the valve leaflets are depicted as simple straight lines in FIG. 3B, in practice the native leaflets typically deform around the periphery of the proximal end of the pump. The native leaflets, positioned as such, may also contribute to improved sealing around the outside of the pump housing. With the blood pump 10 in position through sewing ring 50*a* and pulmonary valve 162, the proximal portion 31*a* of the cylindrical central section of the pump housing extends through sewing ring 50*a*, whereas the leg 14 of cable housing 15 lies distal to ring 50a and distal to the cut end 165a of the artery. The blood pump may be secured to the sewing ring 50a. For example, sewing ring 50a may have a screw adjustment which may be tightened to move a movable wall portion towards a fixed wall portion, as discussed above, which may secure the pump within the sewing ring by clamping the proximal portion 31a of the cylindrical section. This secures the pump within the pulmonary valve 162 as well.

The second sewing ring 50b and second cut end 165b may then be positioned over the distal end of the pump 10, as in FIG. 3B, and the second sewing ring 50b may be secured to the pump in, for example, the same manner as sewing ring 50a, as by clamping around the distal portion 31b of the pump housing central cylindrical section. This securement step may be performed in other ways depending on the type of sewing rings used. Also, in one alternative, the sewing rings may be secured to the pump in reverse order, such that the sewing ring 50b is first placed over the distal end of pump 10 and secured thereto, followed by the sewing ring 50a being placed on the proximal end of the pump 10 and secured thereto. As illustrated, the leg 14 of cable housing 15 may be positioned to extend in a transverse direction away from the pump 10 and between the two sewing rings, such that the cable housing extends outside of the vasculature between the cut ends. The cut ends 165a and 165b optionally may be sutured to one another. The illustrated shape of the cable housing 15 is merely exemplary, and, once outside the vasculature, the cable housing may direct the wiring in any direction, but preferably in the direction of the implanted or external power source.

It should be noted that, as illustrated in FIG. 3B, the native valve leaflets of the pulmonary valve are shown to be inverted by the pump, that is, forced open in a retrograde direction, opposite from which they typically open. This may in part be due to the distal approach of the pump 10 to the valve 162 during implantation. However, the valve leaflets may be forced open in any configuration as practicable. Since the blood pump is effectively replacing the valve in the pulmonary artery, the leaflets are not intended to maintain any of their function, and thus, the surgeon may force open the valve leaflets in any way desired, including such retrograde opening of the leaflets as illustrated. Alternatively, the native valve leaflets may be removed prior to implantation of the pump.

The pump 10, so implanted, desirably is positioned proximal to the bifurcation and through the pulmonary valve. Further, the proximal end of the pump may be positioned just proximal to the pulmonary valve and extend minimally, if at all, into the conus arteriosus, but not beyond the conus arteriosus. The length of the pump 10 is such that this positioning can be achieved since a normal pulmonary artery 160 is about 5 cm in length, and the pump is between about 4 cm to about 5 cm, preferably 4.5 cm. Also, the blood pump 10 is generally dimensioned to have a diameter substantially the same as the diameter of the pulmonary valve and/or pulmonary artery. As such, the blood pump is generally dimensioned to fit within a native heart valve space and can accommodate the entire flow, intended to pass through the native valve, (as mentioned above, typically about 7 liters/minute to about 8 liters/minute). Further, since the blood pump may have substantially the same diameter as the pulmonary valve and/or pulmonary artery, such positioning may provide for a better seal between the wall of the vasculature (and the "opened" native valve leaflets) and the pump attachment device and pump, as well as allow for a maximum diameter flow path through the blood pump.

Additionally, the two ends of the tubular casing of the pump may include a taper 16 such that the diameter $D_2$ along at least a portion of the ends, preferably at the extreme ends 12, 13 of the casing, is less than that of the diameter $D_1$ of the rest of the length of the tubular casing. These tapers may provide the benefit of minimizing, if not substantially eliminating, any contact between the ends of the pump and the surrounding tissue. For example, if the taper on the proximal end of the tubular casing was not present, the edge of such a casing may contact tissue of the heart, such as the wall around the conus arteriosus or the tissue at the connection of the pulmonary artery to the conus arteriosus, which may result in tissue damage. Similarly, for example, if the taper on the distal end of the tubular casing was not present, the edge of such a casing may contact tissue adjacent to the bifurcation 175, similarly resulting in tissue damage. The tapers 16 on both ends need not be identical, such that the length and angle of taper of either or both ends 12, 13 may be different from one another. The exterior surfaces of the pump desirably are devoid of sharp edges. For example, the pump desirably does not have sharp edges at the ends of the conical sections.

Once the pump has been implanted and connected to the power source (FIG. 1), the patient is removed from bypass and pump 10 is started. Once started, the pump desirably runs continuously until removed. The pump aids the native ventricle in impelling blood through the pulmonary circulation. All or substantially all of the blood passing from the right ventricle goes through the pump. The pump acts in place of the native pulmonary valve in preventing retrograde flow during right ventricular diastole.

Figure 4:
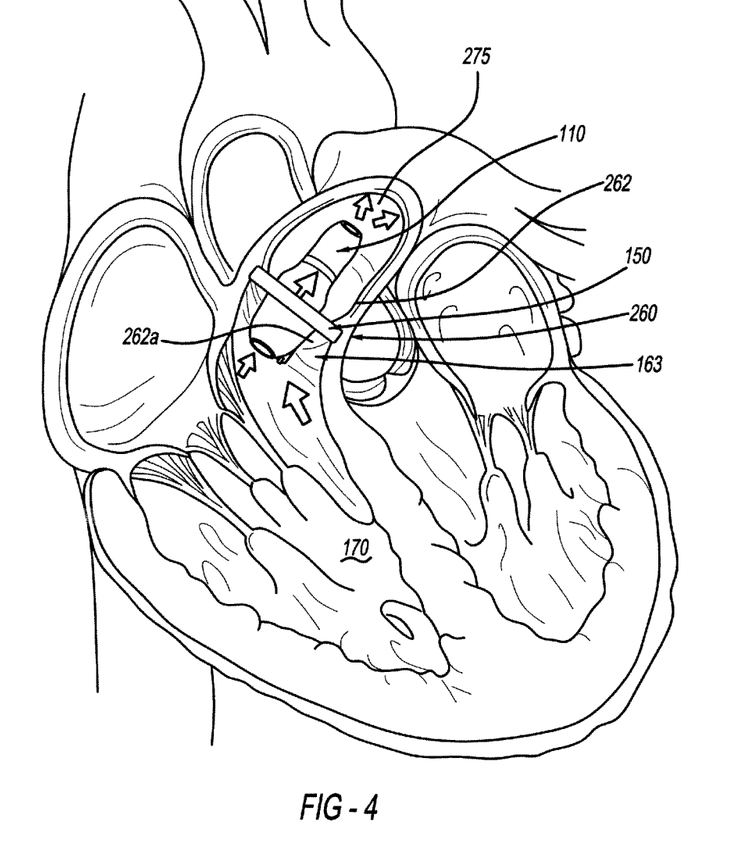
FIG. 4 is a partially sectional view depicting a blood pump according to one embodiment of the present invention installed within a native pulmonary valve space, wherein the native valve space is illustrated in cross-section to illustrate blood pump position.

In another embodiment, the present invention may include, as illustrated for example, in FIG. 4, an apparatus including a blood pump 110, similar to blood pump 10, above. Blood pump 110 may include a cable housing (not shown) similar to the cable housing 15 of blood pump 10 discussed above with reference to FIGS. 1-3B.

A pump attachment device 150, as illustrated, may be include a fabric ring, such as a Dacron® felt ring or the like, and may also include a clamping device such as a ring for securing the fabric ring to the housing of in a manner similar to the sewing rings discussed above. Examples of such fabric rings are disclosed in U.S. Patent Application Publication No. 20070134993, the entirety of which is incorporated by reference herein as if fully set forth herein.

As illustrated in FIG. 4, this apparatus, including blood pump 110 and pump attachment device 150 may be implanted into a native heart valve space. As illustrated, the native heart valve space may be a native pulmonary valve space including a portion of a pulmonary artery 260 encompassing a pulmonary valve 262 and extending from the annulus of native valve 262 to a bifurcation 275 of the pulmonary artery in a distal direction. As depicted, the pump 110 also projects proximally through the annulus of native valve 262 and into the conus arteriosus 163 of a right ventricle 170.

In the implantation procedure, pulmonary artery 260 is again accessed via an open-chest procedure and the patient is placed on heart bypass. A cut may be formed through at least a portion of the sidewall of the portion of the pulmonary artery 260. The cut may completely sever the portion of the pulmonary artery to form two cut ends. Alternatively, the cut may be a circumferential or longitudinal cut through only a portion of the width of the artery, thereby creating a slit rather than completely severing the artery. Other cuts may also be performed so long as access to the pulmonary valve space is obtained and the blood pump (and any pump attachment device) can be implanted through the cut and directed, in a proximal or retrograde direction, such that a portion of the pump is positioned within the annulus of the pulmonary valve, as illustrated in FIG. 4.

After the pulmonary artery is cut, the pump 110 and attachment device 150 may then be placed in the pulmonary artery, so that the pump 110 extends within or adjacent to the pulmonary valve. Specifically, in one example as shown, the implant attachment device is implanted within or adjacent to a native pulmonary valve annulus. As depicted in FIG. 4, the native valve leaflets 262a are deformed in the retrograde or proximal direction, toward ventricle 170, by the pump 110 during the implantation of the pump. The pump attachment device 150 may be secured in place by suturing the felt ring of the attachment device to the annulus of native valve 262 and adjacent tissues. The pump may be secured to the attachment device 150 either before or after implantation. In the implanted condition shown in FIG. 4, the attachment device 150 extends between the exterior of the pump and the interior of the pulmonary artery and annulus. Thus, the attachment device forms a partial or, desirably, complete seal around the exterior of the pump. The native valve leaflets 262 also contribute to the seal. After implantation, the cut in the pulmonary artery is closed, as by suturing. The cable housing (not shown) desirably projects out of the vasculature through the sidewall of the pulmonary artery as discussed above.

In other variants, the pump 110 may then be secured to the pump attachment device 150 through a variety of techniques. For example, the pump 110, on its outer casing, may include eyelets or the like such that the pump can be sewn to the device 150. In this case, attachment device 150 may include only a ring of felt or other suturable material, without a clamping device. Alternatively, the pump 110 may be press-fit into place within the device 150. In yet another alternative, the device 150 may be secured to the pump 110 during manufacture, or at least prior to implantation, using an adhesive or the like, and the device 150 and pump 110 combination may be secured to the native heart valve space simultaneously by suturing the device 150 to the native annulus, or adjacent thereto. In a further variant, the attachment device 150 may be secured to an end of the artery resulting from a cut being formed therethrough, rather than to the annulus.

Figure 5A:
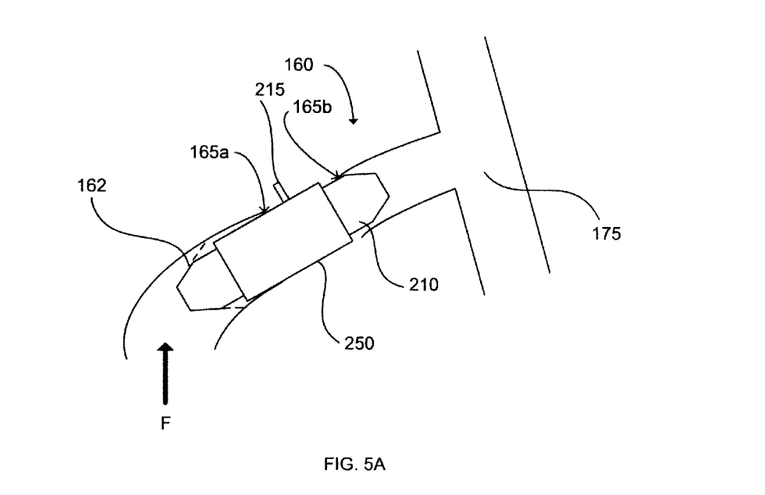
FIGS. 5A and 5B are views similar to FIGS. 2A-3B but depicting another embodiment of a method of implanting a blood pump of the present invention.
Figure 5B:
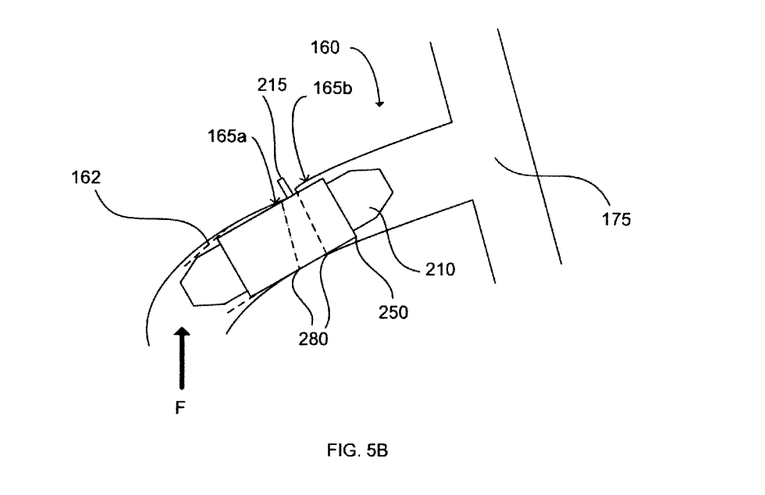

A further embodiment of present invention, as illustrated for example, in FIGS. 5A-5B, uses an apparatus including a blood pump 210, similar to blood pumps 10, 110, above. Blood pump 210 may include a cable housing 215 extending transverse from the tubular casing of the pump, similar to blood pump 10. In this embodiment, the Pump attachment device 250, includes a felt strip 250 formed into a tubular structure attached to the pump and substantially surrounding the pump over at least a portion of its axial length. Strip 250 may have a larger width or axial extent than the above-disclosed felt ring 150 (FIG. 4) such that strip 250 may cover a larger portion of the length of the pump 210. Preferably, strip 250 terminates distal to the proximal end of the pump, so that a portion of the pump casing at the proximal end is not covered by the strip. This larger width felt strip may allow a surgeon to have greater options in deciding where to suture a surrounding tissue to the pump 210. The felt strip is positioned to substantially surround the tubular casing at the juncture of the cable housing 215 with the outer casing of the pump. Thus, a portion of the strip 250 covers the distal portion of the pump casing, whereas another portion of the felt strip covers the proximal portion of the cable housing. Strip 250 is secured to the blood pump 210 prior to surgery, preferably at time of manufacture. For example, strip 250 may be adhesively bonded to the pump casing. Alternatively, though the surgeon or other technician may secure the pump 210 and strip 250 together prior to surgery. The pump, with the strip thereon, is implanted by a procedure similar to that discussed above with reference to FIGS. 2A-3B. Here again, the pump is inserted into the cut ends 165a and 165b of the pulmonary artery. Again, the pump desirably does not extend to the bifurcation 175 of the pulmonary artery, and extends only slightly proximal to the native pulmonary valve 162. However, in the procedure using this embodiment, the sewing rings 50a and 50b (FIGS. 3A and 3B) are not used. Instead, after placing the pump and strip within the cut ends of the pulmonary artery, the pump is secured in place by suturing the cut artery ends 165a, 165b to the strip via sutures 280. Additional sutures may be used at other locations. The cut ends 162a; 162b may be sutured to one another as well.

In this embodiment, strip 250 helps to form a seal around the blood pump substantially blocking flow around the pump. The portion of the pump positioned within the native heart valve annulus may force the native valve leaflets to a substantially open position such that the native valve leaflets abut surrounding tissues and are substantially retained against opening and closing motion. Such a configuration is illustrated in FIG. 5B. In this embodiment as well, cable housing 215 projects out of the artery at between the sutured cut ends.

In a variant, strip 250 may be formed as two separate strips, one disposed proximal to the cable housing and one disposed distal to the cable housing. In yet another variant, the strip may be disposed only proximal to the cable housing or only distal to the cable housing. In such a variant, the strip may be sutured within only one of the cut ends 162a, 162b of the artery.

As discussed above, the pump attachment device of the various embodiments of the present invention may include a felt ring 150, a felt strip 250, an at least one sewing ring 50a, or the like. It is envisioned that any structure capable of securing to both tissue and a blood pump may be used to secure the blood pump of the present invention. Further, in any of the above embodiments, and variations thereof, the pump and pump attachment device may be secured to one another through a variety of different structures. For example, the two structures may be secured to one another through a press-fit, additional suturing between the attachment device and the pump, or the like. In one alternative example, the sewing ring, rather than including the movable and tightenable wall, the ring may instead include, may include a cylindrical ring within the sewing ring, constructed of a solid material such as stainless steel or the like, and an O-ring seal, to form a tighter press-fit with the pump 50 positioned through the sewing ring, cylindrical ring and O-ring.

Alternatively, the blood pump may include an additional structure which engages the pump attachment device. The structure may be a groove on the outer housing within which the attachment device may sit. Another structure may include at least one flange or other structure on the outer housing which is meant to abut the attachment device and hold the pump in place relative thereto. In another alternative, the pump may include an at least one eyelet on the outer housing to which the pump attachment device may be sutured thereto. Other such structures are also envisioned.

In the embodiments discussed above, the cable housing is a substantially rigid element and is structurally distinct from the wiring extending within the cable housing. However, this is not essential. In other embodiments, the cable housing may be flexible and be integrated with the wiring. For example, the cable housing can be the outer covering of a flexible insulated cable. Such a cable may form part or all of the cable which connects the pump to the power source. In yet another variant, a connector may be provided in the casing facing outwardly, transverse to the axis and flow path so that a cable can be connected to the housing during use to provide the electrical connection extending transverse to the axis and flow path.

In further variants, the pump does not have a connection projecting transverse to the axis of the pump as discussed above. Instead, the wiring for connection to a power source, may exit from the housing of the pump in a generally axial direction, as, for example, from the proximal end of the pump. In this case, the wiring used to connect the pump to the power source is directed into the right ventricle. The wiring may extend and to, for example, to the vena cava or other vein and exit from the vascular system at through the wall of the vein. In another alternative, the wiring may exit the heart through the wall of the right ventricle and continue to a power source. Other configurations are also envisioned depending on the particular anatomy, power supply, and needs of a particular patient.

The above various methods for insertion of a blood pump, using the various illustrated embodiments of the blood pump 10, 110, 210 and pump attachment device 50, 150, 250 were described with reference to placement within a native heart valve space in the heart, specifically a pulmonary heart valve space including the pulmonary heart valve 162 and the pulmonary artery 160. However, it should be understood that such methods may also be used for implanting a blood pump in other native valve spaces in the vasculature of the patient, such as in veins, arteries, blood vessels and the like. The above methods may also be used in other native heart valve spaces, such as the aortic valve, for example. However, with regard to the aortic valve, it may be beneficial to position the pump in the aorta, downstream of the valve, and position an extended pump intake cannula, or the like, through the valve and to the left ventricle. Similar steps to implant and secure the pump, as discussed above, may be used.

The various methods of the present invention may be useful in providing right ventricular assist to the heart of a patient, and for treating various cardiovascular diseases and conditions, such as for example valve disease, particularly pulmonary valve disease, or other conditions affecting the pulmonary circulation.

Such various above methods, or similar envisioned methods, may result in a seal around the outer pump housing created by at least the native valve leaflets abutted against the surrounding tissue (e.g., the valve annulus, the sidewall of the pulmonary artery, etc.), the pump attachment device, the suturing between the pump attachment device and the surrounding tissue (e.g., the sidewall of the pulmonary artery), and the connection between the pump attachment device and the blood pump. Such structures are intended to ensure that the full blood flow, from the right ventricle, passes through the flow path in the blood pump and that any flow of blood around the outer housing of the blood pump is minimized if not substantially blocked.

In any of the above methods, it should be noted that, prior to positioning of the pump through the valve, the valve leaflets, and any other adjacent tissue, may be removed from the artery.

In another alternative, since the above methods effectively implant a blood pump in place of a native valve, if the pump is ever removed at a later date, but the heart (and affected valve) remain in the patient (e.g., the patient does not undergo a heart transplant), a replacement valve, as is known in the art, may be implanted in place of the removed blood pump.

The above various methods could also be used in conjunction with a left ventricular assist device used in the left ventricle, to create bi-ventricular heart support. The pump implanted in the pulmonary valve space as discussed above occupies minimal pericardial space. This leaves space for implantation of the left ventricular assist device, so that pumping support can be provided to both the left and right ventricles. While the above methods were described with regard to open-heart chest, and use of bypass, it is envisioned that a pump may be implanted within, for example, the pulmonary artery and pulmonary valve, through a catheter-based procedure. Such procedure may be performed through the vasculature leading to the heart or through a catheter inserted directly into the chest cavity and through the heart wall. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantable intravascular blood pump apparatus comprising:
    an implantable intravascular blood pump having a substantially tubular casing having a tapered proximal end, a tapered distal end and a central section extending a length therebetween, the tubular casing having a first outer diameter along at least a portion of the length, a flow path extending through the tubular casing from the proximal end to the distal end, a rotor within the flow path, a stator within the casing, and a cable housing, wherein the proximal end is adapted to force native valve leaflets of a patient into an open position; and
    a pump attachment device including one of a fabric ring, a fabric strip or a sewing ring secured circumferentially over a curved surface of the tubular casing between the tapered proximal end and the tapered distal end and adapted for fixed attachment to an annulus of a native valve of the patient such that a sidewall of a vasculature extends in two directions from the pump attachment device, wherein the pump attachment device is also adapted to form a seal between the exterior of the pump and the native valve.

2. The apparatus of claim 1, wherein the casing includes a cylindrical section having the first outer diameter.

3. The apparatus of claim 1, wherein the cable housing extends from the tubular casing remote from the proximal and distal ends of the casing.

4. The apparatus of claim 1, wherein the pump attachment device includes at least one of a felt ring, a felt strip, or a sewing ring.

5. The apparatus of claim 4, wherein the at least one sewing ring is two sewing rings.

6. The apparatus of claim 5, wherein when the pump is implanted, the cable housing extends from the tubular casing at a position between the two sewing rings.

7. The apparatus of claim 1, wherein the apparatus is adapted to be positioned within a vessel, and the cable housing extends transverse from the tubular casing, through a wall of the vessel to a position outside of the vessel.

8. The apparatus of claim 1, wherein the cable housing is hollow.

9. The apparatus of claim 8, wherein the cable housing comprises a first leg projecting from the central section, wherein the leg extends in a direction perpendicular to the flow path.

10. The apparatus of claim 9, wherein the cable housing further comprises a second leg projecting in a direction transverse to the first leg, and parallel to the flow path.

11. The apparatus of claim 8, wherein the cable housing further comprises electrical wiring positioned through the hollow cable housing.

12. The apparatus of claim 11, wherein the cable housing further comprises a connector adapted to connect the stator to a power source.

13. The apparatus of claim 1, wherein the proximal end is conical and is adapted to fit within a native heart valve space.

14. The apparatus of claim 1, wherein the valve leaflets are forced open in a retrograde direction.

15. The apparatus of claim 1, wherein the apparatus is adapted to be positioned within a vessel, and the cable housing extends between cut end portions of the vessel.

16. An implantable intravascular blood pump apparatus comprising:

a blood pump having a substantially tubular casing having proximal and distal ends and a central section extending between the proximal and distal ends, the tubular casing having a first outer diameter along at least a portion of the length, a flow path extending through the tubular casing from the proximal end to the distal end, a rotor within the flow path, a stator within the casing, a cable housing, and means for maintaining leaflets of a native valve of a patient in an open position; and a pump attachment device including one of a fabric ring, a fabric strip or a sewing ring secured circumferentially over a curved surface of the tubular casing between the tapered proximal end and the tapered distal end and adapted for fixed attachment to an annulus of a native valve of the patient such that a sidewall of a vasculature extends in two directions from the pump attachment device.

\* \* \* \* \*